United States Patent [19]
Proksch et al.

[11] 3,955,925
[45] May 11, 1976

[54] PREPARATION OF OPTICALLY CLEAR SERUM

[76] Inventors: Gary J. Proksch, 1045 W. 77th St., South Drive; Dean P. Bonderman, 586 W. 77th Drive, North, both of Indianapolis, Ind. 46260

[22] Filed: June 13, 1975

[21] Appl. No.: 586,569

Related U.S. Application Data

[63] Continuation of Ser. No. 414,799, Nov. 12, 1973, abandoned.

[52] U.S. Cl. .............................. 23/230 B; 252/408; 260/112 B
[51] Int. Cl.² .......................................... G01N 33/16
[58] Field of Search ................... 23/230 B; 424/101; 252/408; 260/112 B

[56] References Cited
UNITED STATES PATENTS

| | | | |
|---|---|---|---|
| 2,824,842 | 2/1958 | Sulkowitch | 23/230 B X |
| 3,260,648 | 7/1966 | Fox | 23/230 B X |
| 3,274,062 | 9/1966 | Lou | 252/408 X |
| 3,497,319 | 2/1970 | Altschul | 23/230 B |
| 3,682,835 | 8/1972 | Louderback | 23/230 B X |
| 3,764,556 | 10/1973 | Kuchmak et al. | 252/408 |
| 3,770,631 | 11/1973 | Fekete et al. | 424/101 X |

OTHER PUBLICATIONS

Bernfeld et al., J. Bio. Chem., Vol. 235, No. 10, pp. 2852–2859, Oct. 1960.
Oncley et al., J. Amer. Chem. Soc., Vol. 79, No. 13, pp. 4666–4671, July 1957.
Jonas, J. Bio. Chem., Vol. 247, No. 21, pp. 7767–7772, Nov. 1972.

*Primary Examiner*—Morris O. Wolk
*Assistant Examiner*—Arnold Turk
*Attorney, Agent, or Firm*—Woodard, Weikart, Emhardt & Naughton

[57] ABSTRACT

A stable optically clear serum is prepared for use in the preparation of standards and quality control reference material for the assay of human serum components. Prebeta lipoproteins, beta lipoproteins and chylomicrons are removed from human serum by specific precipitation. The serum resulting from the process disclosed retains its optical clarity upon freezing, lyophilization and reconstitution with aqueous media. Bovine lipoproteins are added to restore desired levels of cholesterol and triglycerides.

19 Claims, No Drawings

PREPARATION OF OPTICALLY CLEAR SERUM

This is a continuation, of application Ser. No. 414,799, filed Nov. 12, 1973 now abandoned.

BACKGROUND OF THE INVENTION

1. Field of the Invention:

This invention relates to removal of chylomicrons, prebeta lipoproteins, and beta lipoproteins from human serum or plasma to prepare a stable optically clear serum.

2. Description of the Prior Art:

The use of pooled human serum or plasma in the preparation of chemical standards and quality control reference material for the assay of human blood serum constituents is well known. This pooled human serum or plasma is commonly stored as a dry powder after freezing or lyophilization to be reconstituted at the time of use. However, when lyophilized human serum or plasma is reconstituted with aqueous media, the resulting solution possesses variable amounts of turbidity, even though the original serum or plasma was optically clear. This turbidity produced upon reconstitution of lyophilized serum interferes with the analytical measurement of serum constituents.

Several patents disclose precipitation techniques for removing proteins from serum or plasma. Sample patents teaching such techniques are U.S. Pat. No. 2,922,745 (1960) to Singher et al, U.S. Pat. No. 3,560,475 to Fekete et al, (1971), and U.S. Pat. No. 3,682,881 (1972) to Fekete et al. While these patents do in fact disclose protein precipitation methods, in general, the procedures prevent the use of the remaining serum as a standard for certain tests and do not lend themselves readily to large scale processing, others yield crude products by modern standards and in still others the overall yields are low.

A method for removal of lipoproteins from serum by specific precipitation is disclosed by Burstein, Scholnick, and Morfin in *The Journal of Lipid Research*, Volume 11 (1970), pages 583–595. This method, however, is directed towards obtaining lipoproteins in purified form and makes no mention of additional steps needed to be done to the serum for its use as a standard.

SUMMARY OF THE INVENTION

One aspect of this invention relates to a method of preparing a lyophilized human serum product which, upon reconstitution, completely dissolves in water within a short time span, i.e. less than 30 minutes, contains the major normal human plasma constituents in desired concentrations, and is optically clear upon reconstitution with aqueous media. The serum material is prepared by the selective precipitation and removal from human serum of chylomicrons, unstable very low density lipoproteins (pre beta lipoproteins), and low density lipoproteins (beta lipoproteins). In some embodiments of the invention, the lipid, cholesterol, and triglyceride levels of the serum which are reduced by this precipitation are restored to desired levels by the addition of soluble derivatives or by the addition of stable lyophilizable lipoproteins from animal sources such as bovine lipoproteins.

The lyophilized serum of this invention is particularly suitable as a base material for the preparation of standards and quality control reference material for the assay of human serum components. The process of this invention comprises mixing a human serum sample with a metal cation selected from the group consisting of calcium, manganese, and magnesium. A polysulfate derivative is added to this mixture which precipitates lipoprotein polysulfate complexes, which contain chylomicrons, pre-beta lipoprotens and beta lipoproteins. These complexes are then separated from the clear supernatant by means of precipitation. A precipitating agent such as oxalate is then added to precipitate the remaining metal cation from the clear supernatant. The resulting clear supernatant is freeze dried or lyophilized for storage until use. Upon reconstitution with aqueous media the lyophilized serum of this invention is optically clear and is completely soluble in an aqueous media.

It is therefore an object of this invention to provide a process for making a serum standard which incorporates the specific precipitation of chylomicrons, pre-beta lipoproteins, and beta lipoproteins from blood serum.

It is an additional object of one aspect of this invention to produce a blood serum which retains its optical clarity upon freezing, lyophilization and reconstitution with aqueous media.

It is a further object of one aspect of this invention to provide a lyophilized serum which, upon reconstitution, is readily soluble in water in a short period of time.

It is a still further object of one aspect of this invention to provide a lyophilized product which retains its optical clarity and at the same time contains all the normal major human blood plasma constituents.

It s a still further object of one aspect of this invention to prepare a serum standard from outdated citrated human whole blood.

It is an additional object of one aspect of this invention to prepare an optically clear cholesterol standard using bovine lipoproteins.

It is a still further object of another aspect of this invention to prepare an optically clear triglyceride standard using bovine lipoproteins.

These and other objects of this invention will be made obvious by the following disclosure of the preferred embodiment.

DETAILED DESCRIPTION OF THE PREFERRED EMBODIMENT

Human serum or plasma contains four major classes of lipoproteins. These are chylomicrons, very low density lipoproteins (pre beta lipoproteins), low density lipoproteins (beta lipoproteins), and high density lipoproteins (alpha lipoproteins). The actual content for samples varies from one to the other with respect to certain physical and chemical parameters. Lipoproteins are a complex of a protein with a lipid. The problem associated with lipoproteins is that they tend to cause serum turbidity. This turbidity makes accurate use of standard turbidimetric or colorimetric measuring devices virtually impossible. Removal of the chylomicrons, pre-beta lipoproteins, and beta lipoproteins has been found to result in a serum which retains its optical clarity upon freezing, lyophilization and reconstitution with aqueous media.

The actual starting substance of the disclosed procedure is the obtaining of plasma which is defined as the liquid part of the blood containing fibrinogen. To obtain normal human plasma, samples are obtained by pooling approximately equal volumes of the liquid portions of whole blood from not less than eight adult humans. Outdated citrated whole human blood, which is old whole blood to which citrate, phosphate, and dextrose have been added, is used if available in view of its low cost. From this pooled blood, normal human plasma serum is extracted. The serum is the clear, amber, alkaline fluid of the blood from which cellular elements have been removed by clotting. The serum contains the salts, soluble protein, and lipoproteins. The lipoproteins are rich in triglycerides and cholesterol.

After the plasma or serum has been obtained, a metal cation is added. Metallic cations which have been found acceptable include calcium, magnesium and manganese. Optimum concentrations for the metal cation are from 0.001 molar to 1.00 molar. After the metal cation has been added and has gone into solution, the pH of the resulting mixture is preferably adjusted to from about 7.0 to about 8.0, and more preferably 7.4. This pH adjustment is accomplished by the use of either sodium hydroxide or hydrochloric acid depending of course on the pH of the initial mixture. 6.0 normal solutions of either sodium hydroxide or hydrochloric acid are preferred.

Next a polysulfate is added to the cation-serum mixture. Ideally, the polysulfate should be added while the temperature is between 0° C and 37° C while the pH remains at from about 7.0 to about 8.0. Polysulfates which have been found acceptable include dextran sulfate, polyvinyl sulfate sulfated amylopectin, heparin, and other polysulfated polymers. The polymer must have a molecular weight of at about 10,000, preferably at least 100,000, and should have at least one sulfate group per monomer. This results in flocculant lipoprotein-polysulfate complex precipitant containing chylomicrons, pre-beta lipoproteins and beta lipoproteins. The precipitant is removed and either discarded or stored for later use. Next the pH of the supernatant is preferably adjusted to from about 6.5 to 8.5 using as before either sodium hydroxide or hydrochloric acid solutions.

A precipitating agent, preferably oxalate, is then added if it is desired to remove any excess cation. Alternatively, carbonate, phosphate, citrate, or succinate are used as a precipitating agent. For optimum results, the precipitating agent concentration should be from about 0.001 molar to about 0.5 molar. The resulting precipitate is removed and discarded. If the serum originally used was obtained from citrated whole human blood, the supernatant is dialyzed against physiological saline to remove excess glucose, citrate and phosphate which are present. Electrolytes, bilirubin, glucose and other compounds which have been removed are then added back to the dialyzed serum to achieve desired (normal) levels. At this point, the serum is optically clear and is ready either for immediate use or for lyophilization. Most commonly lyophilization will be the route followed. To prepare an abnormal serum standard, constituents such as enzymes, proteins and polysaccharides are added to the normal serum preparation to achieve a desired abnormal assay.

Lyophilization may be accomplished by any of several well known techniques. When lyophilized, the serum is stable for several months at 5° C. Upon reconstitution of the lyophilized powder with aqueous media, the material rapidly solubilizes (typically within 10 minutes) and is optically clear. Typically, less water is added upon reconstitution than was removed by lyophilization to increase protein concentration. This optically clear solution is in contrast to the results of prior methods of serum lyophilization and storage where excess turbidity develops upon reconstitution with aqueous media.

With removal of the pre beta lipoproteins, beta lipoproteins and chylomicrons by this process, it is found that normal levels of triglycerides and cholesterol are significantly reduced. These constituents are, of course, important in that they are used in many tests as health indicators. Therefore the triglyceride and cholesterol levels are optionally restored to normal or even elevated levels by one of several methods. First, water soluble triglycerides with a low vapor pressure so that they are not substantially removed by lyophilization, such as trichloroacetate triglyceride, trihemisuccinate glycerol, and soluble cholesterol derivatives such as potassium cholesterol hydrogen succinate may be directly added to the serum prior to lyophilization. Secondly, water soluble but volatile triglycerides such as glycerol triacetate or glycerol tripropionate and a soluble cholesterol derivative such as potassium cholesterol hydrogen succinate may be added to the serum after lyophilization in the aqueous reconstitution diluent.

The serum from fasting animals, such as bovine, was observed to retain its clarity upon lyophilization and reconstitution with water thus indicating that the lipoproteins from certain animal sources were more stable to lyophilization than human chylomicrons, pre-beta lipoproteins, and beta lipoproteins. Therefore, isolated bovine lipoprotein fractions containing cholesterol and triglycerides can be added to the treated human serum to achieve the desired cholesterol and triglyceride levels prior to or after lyophilization. Upon reconstitution of the dry powder with water, the material rapidly solubilizes, generally within thirty minutes, and is optically clear. Thus, the preferred method of restoring the triglyceride and cholesterol levels to human blood serum is by the addition of bovine lipoprotein fractions containing cholesterol and triglyceride prior to lyophilization of the human serum.

EXAMPLE 1

A normal 1000 ml. pooled human blood plasma sample was obtained, and calcium chloride was added to achieve a 0.06 molar concentration of calcium cation in the plasma. The pH was adjusted to 7.4 using 1.5 ml. of $6N$ NaOH. The mixture was then heated to 37° C and one ml. of topical bovine thrombin (1000 NIH units per ml.) was added. The plasma was allowed to clot and the serum was then expressed from the clot. Dextran sulfate was added to the serum to achieve a concentration of 5 g/l. A flocculant lipoprotein-complex precipitate was formed at pH 7.4, the precipitate containing chylomicrons, pre-beta lipoproteins, and beta lipoproteins.

The precipitate was subsequently removed and discarded. The resulting supernatant serum was optically clear.

The serum was freeze dried to a powder form and stored at 5° C for 40 weeks. After storage, distilled water was added to reconstitute the serum. The serum, 10 minutes after reconstitution with water, was optically clear.

EXAMPLE 2

The identical procedure as was followed in Example 1 was followed with a single exception. Prior to freeze drying, a bovine lipoprotein extract was added to substitute for the human chylomicrons, pre-beta lipoproteins, and beta lipoproteins that were removed and to bring the cholesterol level to the desired level.

After storage exactly as in Example 1, excellent clarity results were obtained.

The bovine lipoprotein extracts were obtained in the following manner. To bovine serum, calcium chloride was added to achieve a 0.05 molar Ca cation concentration. Dextran sulfate was added to achieve a 0.5 g/l concentration. While water soluble phosphotungstate or another polymer having a molecular weight of 10,000 and at least one sulfate group per monomer have been found to work, dextran sulfate is preferred. The resulting precipitate contained low density lipoprotein and was removed and saved. To the remaining serum, additional calcium chloride was added to achieve a concentration of 0.2 molar. An additional dextran sulfate was added to achieve a concentration of 2.5 g/l. The resulting precipitate was removed and consisted of essentially a complex of dextran sulfate and high density lipoprotein material. This second precipitate complex of bovine lipoprotein and dextran sulfate is dissolved in 50 ml. of 10% sodium bicarbonate solution. Any precipitates which form are removed and discarded. The supernatant is dialyzed against water and then one percent $BaCL_2$. Any precipitates which form are removed and discarded. The supernatant is then again dialyzed against water. This final purified bovine lipoprotein solution, which had a concentration of 20 g/l cholesterol, was added to the human serum in an amount sufficient to achieve a standard cholesterol level of 2 g/l in human serum. This is added immediately prior to lyophilization.

EXAMPLE 3

The procedure of Example 2 was followed exactly except the first bovine precipitate fraction was additionally processed and added prior to adding the final lipoprotein fraction to additionally achieve normal triglyceride and cholesterol levels in human serum.

This first precipitated complex of bovine lipoprotein and dextran sulfate is dissolved in 10 ml. of 10% sodium bicarbonate solution. Any precipitates which form are removed and discarded. The supernatant then dialyzed against water and then one percent $BaCl_2$. Any precipitates which form are removed and discarded. The solution is then dialyzed against water to achieve after storage exactly as in Example 1, excellent clarity results were obtained.

EXAMPLES 4–6

The procedure of Examples 1-3 was followed except that after the precipitate was removed and discarded, the supernatant serum was adjusted to pH 7.0 with $6N$ HCl. Sodium oxalate was added to achieve a 0.05 molar concentration. The calcium oxalate precipitate which formed was removed and discarded.

EXAMPLES 7–12

The procedure of Examples 1-6 was followed except that the blood used was outdated citrated whole human blood. Additionally, just before freeze drying, the serum was dialyzed against physiological saline. Subsequently, the serum was brought to normal values of electrolytes and other ingredients by the addition of $HCO_3^=$, $Na^+$, $K^+$, $Cl^-$, $PO_4^=$, glucose, bilirubin, $Ca^{++}$, $Mg^{++}$, uric acid, urea, sulfate, and creatinine.

EXAMPLES 13–24

The procedure of Examples 1-12 was followed using polyvinyl sulfate with a molecular weight of 100,000. Excellent results were achieved.

EXAMPLE 25

The procedure of Example 2 was followed to obtain the second precipitated complex of bovine lipoprotein and dextran sulfate. One half of the complex was purified to obtain pure bovine lipoprotein according to the purification procedure of Example 2. A first reference solution consisted of the sodium bicarbonate solution of dextran sulfate and lipoprotein of Example 2. A second reference solution was made up by adding to water the purified lipoprotein solution of Example 2. The solutions were added to water to achieve 2 g/l cholesterol as assayed by the Leiberman-Burchard method.

A portion of each of these solutions was stored for two months at 5° C and assayed. No change in concentration was noted and the solutions remained clear. Another portion of each of these solutions was lyophilized and reconstituted one year later. No change in concentration of the second reference solution was noted, but difficulty in lyophilization and reconstitution caused a 5% reduction in value when the first reference solution was reassayed.

The second reference solution was then used routinely for 6 months as a reference for assaying human serum for cholesterol. No difficulties were noted.

EXAMPLE 26

The procedure of Examples 2 and 3 was followed to obtain the first precipitated complex of lipoprotein and dextran sulfate. One half of the complex was purified to obtain pure bovine lipoprotein according to the purification procedure of Example 3. A first reference solution was made up by adding the first precipitated complex of dextran sulfate and lipoprotein to 40 ml. of 10% sodium bicarbonate solution. A second reference solution was made up by adding to water the purified lipoprotein. These solutions were added to water to achieve 5.5 g/l triglyceride as assayed by the method of Levy, A. L. and Keyloun, C. *CLIN. CHEM.*, 17, 640 (1971).

A portion of each of these solutions was stored for two months and assayed. No change in concentration was noted and the solutions remained clear. Another portion of each of these solutions was lyophilized and reconstituted one year later. No change in concentration of either solution was noted, and the reconstituted solution was clear.

Each of these reference solutions were used routinely for 6 months as a reference for assaying human serum for triglyceride. No difficulties were noted.

The invention claimed is:

1. A process for preparing a lyophilized serum standard or reference material for the assay of human blood comprising:
   a. mixing human serum with a metal cation selected from the group consisting of calcium, manganese and magnesium;
   b. adding to the serum containing said added metal cation a quantity of polysulfate sufficient to precipitate a lipoprotein-polysulfate complex said polysulfate being a polymer having a molecular weight of at least 10,000 and having at least one sulfate group per monomer;

c. removing said lipoprotein-polysulfate complex precipitate from the serum; and d. lyophilizing the serum from which said lipoprotein-polysulfate complex has been removed.

2. The process of claim 1 in which said polysulfate is polyvinyl sulfate.

3. The process of claim 1 in which said polysulfate is dextran sulfate.

4. The process of claim 1 in which said serum is obtained from citrated whole human blood.

5. The process of claim 1 in which said serum is obtained from a plurality of human donors.

6. The process of claim 1 which additionally includes after removing said lipoprotein-polysulfate complex precipitate from the serum and prior to lyophilization of the serum:
 1. dialyzing the serum and
 2. adding back to the dialyzed serum several of the ingredients which were removed by the dialysis.

7. The process of claim 1 wherein said human serum is derived from plasma by a process comprising:
 a. adding topical bovine thrombin to the plasma,
 b. allowing the plasma to clot, and
 c. separating the serum from said clot.

8. The process of claim 1 in which said metal cation is magnesium.

9. The process of claim 8 which additionally includes after removing said lipoprotein-polysulfate complex precipitate from the serum, and prior to lyophilization of the serum:
 1. adding a precipitating agent to the serum to precipitate said magnesium and
 2. removing the precipitant.

10. The process of claim 1 which additionally includes after removing said lipoprotein-polysulfate complex precipitate from the serum and prior to lyophilization of the serum:
 the step of adding to the serum a lipoprotein fraction extracted from bovine serum.

11. The process of claim 10 in which said lipoprotein fraction extracted from bovine serum is obtained by:
 a. mixing bovine serum with a metal cation selected from the group consisting of: calcium, manganese, and magnesium
 b. adding to the mixture a quantity of polysulfate sufficient to precipitate a lipoprotein-polysulfate complex; and
 c. separating said complex from said bovine serum.

12. The process of claim 1 in which said metal cation is calcium.

13. The process of claim 12 which additionally includes after removing said lipoprotein-polysulfate complex precipitate from the serum, and prior to lyophilization of the serum:
 1. adding a precipitating agent to the serum to precipitate said calcium and
 2. removing the precipitant.

14. The process of claim 13 in which said precipitating agent is selected from the group consisting of: oxalate, phosphate, succinate, carbonate and citrate.

15. The process of claim 1 which additionally includes after removing said lipoprotein-polysuflate complex precipitate from the serum and prior to lyophilization of the serum;
 1. adding a precipitating agent to the serum to precipitate said metal cation and
 2. removing the precipitant.

16. The process of claim 15 in which said precipitating agent is selected from the group consisting of: oxalate, phosphate, succinate, carbonate and citrate.

17. The process of claim 16 in whlch said precipitating agent is oxalate.

18. A lyophilized human serum for use as a standard or reference material in assaying human blood, said lyophilized human serum having essentially all of its normally present pre-beta lipoproteins, beta lipoproteins and chylomicrons removed but containing essentially all alpha lipoproteins and other non-volatile serum components.

19. The lyophilized serum of claim 18 wherein said lyophilized serum additionally includes lipoproteins extracted from bovine serum.

* * * * *